United States Patent [19]

Anderson et al.

[11] Patent Number: 4,686,368
[45] Date of Patent: Aug. 11, 1987

[54] APPARATUS AND METHOD FOR READING TWO-DIMENSIONAL ELECTROPHORETOGRAMS CONTAINING β-RAY-EMITTING LABELED COMPOUNDS

[75] Inventors: Herbert L. Anderson, Santa Fe; W. Wayne Kinnison; John W. Lillberg, both of Los Alamos, all of N. Mex.

[73] Assignee: The United States of America as represented by the United States Department of Energy, Washington, D.C.

[21] Appl. No.: 728,965

[22] Filed: Apr. 30, 1985

[51] Int. Cl.[4] ................................................. G01T 1/00
[52] U.S. Cl. .................................... 250/374; 250/375; 250/385; 250/394
[58] Field of Search ................... 250/385 R, 375, 374, 250/369, 388, 394

[56] References Cited

U.S. PATENT DOCUMENTS 4,431,921  2/1984  Filthuth ............................... 250/374

OTHER PUBLICATIONS

E. Tums, G. Gloeckler, C. Y. Fan, J. Cain and R. Sciambi, "Instrument to Measure Energy and Charge of Low Energy Interplanetary Particles" *IEEE Transactions on Nuclear Science*, vol. NS-21, No. 1, (Feb. 1974), pp. 210–217.

*Primary Examiner*—Janice A. Howell
*Assistant Examiner*—Constantine Hannaher
*Attorney, Agent, or Firm*—Samuel M. Freund; Ray G. Wilson; Judson R. Hightower

[57] ABSTRACT

Apparatus and method for electronically reading planar two dimensional β-ray emitter-labeled gel electrophoretograms. A single, flat rectangular multiwire proportional chamber is placed in close proximity to the gel and the assembly placed in an intense uniform magnetic field disposed in a perpendicular manner to the rectangular face of the proportional chamber. Beta rays emitted in the direction of the proportional chamber are caused to execute helical motions which substantially preserve knowledge of the coordinates of their origin in the gel. Perpendicularly oriented, parallel wire, parallel plane cathodes electronically sense the location of the β-rays from ionization generated thereby in a detection gas coupled with an electron avalanche effect resulting from the action of a parallel wire anode located therebetween. A scintillator permits the present apparatus to be rendered insensitive when signals are generated from cosmic rays incident on the proportional chamber. Resolution for concentrations of radioactive compounds in the gel exceeds 700 μm. The apparatus and method of the present invention represent a significant improvement over conventional autoradiographic techniques in dynamic range, linearity and sensitivity of data collection. A concentration and position map for gel electrophoretograms having significant concentrations of labeled compounds and/or highly radioactive labeling nuclides can generally be obtained in less than one hour.

11 Claims, 3 Drawing Figures

APPARATUS AND METHOD FOR READING TWO-DIMENSIONAL ELECTROPHORETOGRAMS CONTAINING β-RAY-EMITTING LABELED COMPOUNDS

This invention is the result of a contract with the Department of Energy (Contract No. W-7405-ENG-36).

BACKGROUND OF THE INVENTION

The present invention relates generally to an apparatus for reading flat, two-dimensional gel electrophoretograms, and more particularly, to the use of a proportional chamber radiation detector having two-dimensional particle location capability to electornically read a two-dimensional gel electrophoretogram which has been labeled with β-ray-emitting compounds.

Two-dimensional electrophoresis has been increasingly used in a wide variety of studies involving the detection and analysis of proteins from complex biological systems. The technique holds promise for determining, at a molecular level, how living cells work. See, e.g., "The Proteins of Oncogenes," by Tony Hunter, Scientific American 251, 70, (1984), and, in particular, the figure on page 76 thereof for a brief description of gel electrophoretic analysis of proteins. In the technique of two-dimensional electrophoresis, the proteins are separated according to isoelectric pH point by isoelectric focusing in one dimension, and according to molecular weighty by sodium dodecyl sulfate in the second dimension at right angles to the first. Since these two parameters are uncorrelated, it is possible to obtain a quantitative distribution of protein spots over a two-dimensional gel. The location and intensity of each spot is generally made visible by autoradiography when it is desired to evaluate the entire pattern. Often, large numbers of proteins are present, and the amount of potential information contained within a single two-dimensional gel is large. Although progress has been made in automating the procedures involved and in the computer analysis of the patterns obtained, densitometry measurements of a autoradiograph suffer from a number of problems inherent in the photographic process. First, the photographic emulsion is relatively insensitive to β-particles from $^{14}C$ and $^{35}S$, two commonly used radioisotopes for labeling proteins. A deposition of approximately 20,000 disintegrations per $mm^2$ is needed to produce a minimally detectable image. In practice, a gel containing about $10^6$ dpm of a total protein preparation will require an exposure time of about one week. Moreover, protein concentration present in a typical cell under investigation have been estimated to range over six orders of magnitude. Such a dynamic range far exceeds the usable optical density range of photographic film, and requires that a graded series of exposures be obtained for each gel. Exposure times of three or four weeks are not uncommon where species occurring in low abundance are of interest, and the resulting exposures are often unreadable over large areas due to the effects of overexposure from more abundant species. This results in the loss of information for some of the proteins present in smaller quantities within these overexposed areas. Although the total number of proteins estimated to exists in a human cell is about 50,000, only 1 to 3% have been studies in reasonable detai. In view of the importance of proteins in life processes and their potential role in the diagnosis and treatment of diseases, an instrument that is capable of expeditious protein anaylsis with high sensitivity would have significant influence on the development of this important field of investigation.

In "Simple Electronic Apparatus for the Analysis of Radioactively Labeled Gel Electrophoretograms," U.S. Pat. No. 4,311,908, issued to Konstantin Goulianos, Karen K. Smith, and Sebastian N. White on Jan. 19, 1982, the inventors describe a high resolution position-sensitive radiation detector for analyzing the radiation emanating from a β-ray-labeled gel electrophoretogram. A coil used for ionization detectio, also seves as a delay line for determining the location of ionization produced in the vicinity of an anode wire along this anode wire. The geometrical error in determining the point at which a particular β-ray emerges from the gel source is reduced by making the distance between the gel and the anode wire very short and by using the well-known "magic" gas mixture which maximized the number of ion pairs created by the emerging β-rays as they pass through the ionization detection apparatus. In this manner the inventors state that a uniform resolution of about ±0.5 MM at the surface of the gel can be achieved by their invention. However, the location of the source of the β-ray in the gel is determined iń only one dimension according to the teachings thereof.

In "High Accuracy, Bidimensional Read-Out of Proportional Chambers with Short Resolution Times," by A. Breskin, G. charpak, C. Demierra, S. Majewski, A. Policarpo, F. Sauli, and J. C. Santiard, 143 Nucl. Instrum. Meth. 29 (1977), the authors disclose the use of a multiwire proportional chamber having orthogonal cathode strips to determine the two-dimensional charge centroid of an avalanche produced by the interaction of β-rays with a target gas in the region of a nearby anode which induces positive charges thereon. For a ionizing beam of normal incidence to the plane of the cathodes, a resoltuion of about 200 μm is reported. The resoltuion of incident ionizing particles at higher angles is improved by electronically decreasing the observation time of the generated signal. However, since the device described therein is used to accurately determine particle tracks where few particles are emerging from the same location, no concern is given to narrowing the distribution of incident particles. That is, in the situation where large numbers of particles are isotropically emitted from a single, albeit somewhat diffuse source, such as a labeled protein on a gel, the signals generated therefrom in the multiwire proportional chamber will in general be impossible to analyze unless the divergence of the particles is reduced so that their origin can be more clearly identified.

P. G. Seiler, R. Dietlicher, G. Wemmers, M. Salzmann, and A. Moline in "Two-Dimensional Measurement of Pion-Induced Beta Activity in Extended Foils," 27 Phys. Med. Biol. 709 (1982), describe a procedure for improving the spatial resolution of the two-dimensional measurement of the initial location of β-rays in a foil using multiwire proportional chamber technology. Therein, the authors show that the application of a strong magnetic field perpendicular to the foil under investigation and simultaneously passing through the two proportional chambers utilized therefor in a perpendicular manner relative to the planar multiwire electrodes upon which the two dimensional measurements are made, dramatically improves the resoltuion of the measurements. The β-rays are emitted isotropically from the foils and, due to the finite thickness of the proportional chambers, the β-rays are measured at some distance from their origin. These two factors contribute to the smearing of the resulting electronically derived distribution and correspondingly poor ultimate resolution. The β-rays are constrained to move in a helical path with decreasing radius under the influence of the magnetic field as they lose energy by collisions with the detection gas utilized in the proportional chamber, thereby more accurately preserving the coordinates of their origin within the film. The positions of the decaying nuclei can be determined with an accuracy of about 2.5 mm according to the authors.

Seiler et al., supra, also describe the compensation for cosmic radiation. To achieve this goal, two proportional chambers are employed; one on each side of the film under investigation, and parallel thereto. Thus cosmic rays entering one proportional chamber and causing a signal to be generated therein will most likely enter the second proportional chamber and cause a signal therein a short time thereafter. Such coincident pairs of signals are rejected by the logic circuitry employed. Similarly, pairs of near coincident β-ray signals occurring in the opposingly disposed proportional chambers will be rejected. However, one advantage of the Seiler et al. technique is that one may obtain the absolute activity and a profile of the radioactive sources within the thin foil under investigation twice as efficientlysince the β-rays are emitted and detected both above and below the film.

Accordingly, it is an object of the present invention to provide an apparatus and method for accurately reading planar gel electrophoretograms which ahve been labeled with β-ray-emitting compounds.

Another object of our invention is to provide an apparatus and method for permitting measurements to be made on planar gel electrophoretograms which have been labeled with β-ray-emitting compounds in the presence of unwanted stray cosmic ray events.

Yet another object of the present invention is to provide an apparatus and method for quantitatively and linearly reading planar gel electrophoretograms which have been labeled with β-ray-emitting compounds having a wide range of concentrations thereof.

Additional objects, advantagegs and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may include a single flat and rectangular proporitnal chamber radiation detector for receiving and determining the two dimensional coordinates of β-rays emitted from the flat gel electrophoretogram located in close proximity to the flat gel electrophoretogram and parallel thereto, a flat and rectangular scintillator located in close proximity to the proportional chamber and parallel thereto for receiving and detecting cosmic rays in order to permit the β-ray measurements to be made in the presence of such events by rendering the measurement system insensitive thereto, and a means for generating an intense, uniform magnetic field into which the proportional chamber and the scintillator are placed such that the magnetic field lines pass approximately perpendicularly through the rectangular dimension thereof, whereby the β-rays emitted from the gel electrophoretogram in the direction of the proportional chamber are cuased to move in a helical path with decreasing radius as the β-rays are slowed by collisions with a detection gas located in the proportional chamber, thereby accurately preserving the two dimensional coordinates of the source of the β-rays in the gel. Preferably, the proportional chamber is a parallel plane multiwire, two cathode, one anode design. It is also preferred that the proportional chamber be interposed between the gel electrophoretogram and the scintillator.

In a further aspect of the present invention, in accordance with its objects and purposes, the method hereof may nclude placing the flat labeled gel electrophoretogram in a uniform strong magnetic field such that the emitted β-rays execute tight helical motion as they travel in the direction of the magnetic field lines, thereby substantially preserving the two dimensional coordinates of their origina in the gel electrophoretogram, and electronically detecting each of the β-rays emerging from one sige of the gel electrophoretogram, thereby generating a distribution of the two dimensional coordinates thereof which can be related to the origin of the β-rays in the electrophoretogram and consequently to the location and intensity of the labeled compounds therein. It is preferred that the β-rays be caused to collide with a gas which facilitates the formation of charged particles, and whereby the β-rays travel in increasingly tight helices as a result of loss of energy through collisions with the gas. Preferably, the charged particles so produced are accelerated in order to produce electron avalanches which assist in the electronic detection stop. It is also preferred that the electronic detection step is rendered insensitive to the effects of incident cosmic rays.

Benefits and advantages of the present invention include the ability to rapidly determine, with high resoltuion, the two-dimensional intensity distribution of β-ray-emitting labeled compounds on planar gel eletrophoretograms compensated for the effects of unwanted cosmic ray events using a single multiwire proportional chamber β-ray detection apparatus. Direct counting represents a significant improvement over photographic processing which is both insensitive and nonlinear.

BRIEF DESCRIPTION OF THE DRAWINGS

The accompanying drawings, which are incorporated in and form a part of the specification, illustrate one embodiment of the present invention and, together with the description, serve to explain the principles of the invention. In the drawings.

DETAILED DESCRIPTION OF THE INVENTION

Briefly, the present invention utilizes multiwire proportional chamber for the direct quantification of β-ray-emitting labeled compounds on two-dimensional gel electrophoretograms. The data acquisition system includes a scintillation detector to identify and reject signals resulting from external unwanted radiation and a computer which is programmed to accept only events with an appropriate response on adjacent wires in both the x and y coordinates in order to insure low background. The counting chamber, the scintillator and the gel electrophoretogram are located in a strong magnetic field which causes the emitted β-rays to be directed into helical patterns of small diameter. Collisions of the β-rays with gas molecules encountered in the proportional chamber slow these energetic particles down and the helical patterns tend to have decreasing radii as the β-rays progress through the proportional chamber, thereby preserving, to a large extend, the location of the origin of the individual β-ray emissions. Actually, the β-rays are emitted in $4\pi$ radians of solid angel but except for β-rays emitted from the more energetic radioactivate nuclei, most of the emitted radiation will not pass through the substrate supporting the gel, and therefore the measurements are performed only one side of the electrophoretogram with a single proportional chamber. Data is collected with significant efficiency in digitized form which is suitable for ready retrieval in a number of display formats and ready comparisons among gels. A typical two-dimensional gel with reasonable concentrations of labeled compounds and/or highly radioactive labeling nuclides can be read in about one hour. If additional low concentration components are present in the gel, they can often be detected by increasing the counting time since the linearity inherent in direct counting is well-suited to the accurate characterization of groups of close-lying concentrations of compounds. Moreover, the pulse heights of isotopes with different energy β-ray emissions can be discriminated, thereby permitting multiply labeled compounds and compounds bearing different labels to be simultaneously analyzed in situations where there is significant overlap of several important labeled compounds.

Figure 1:
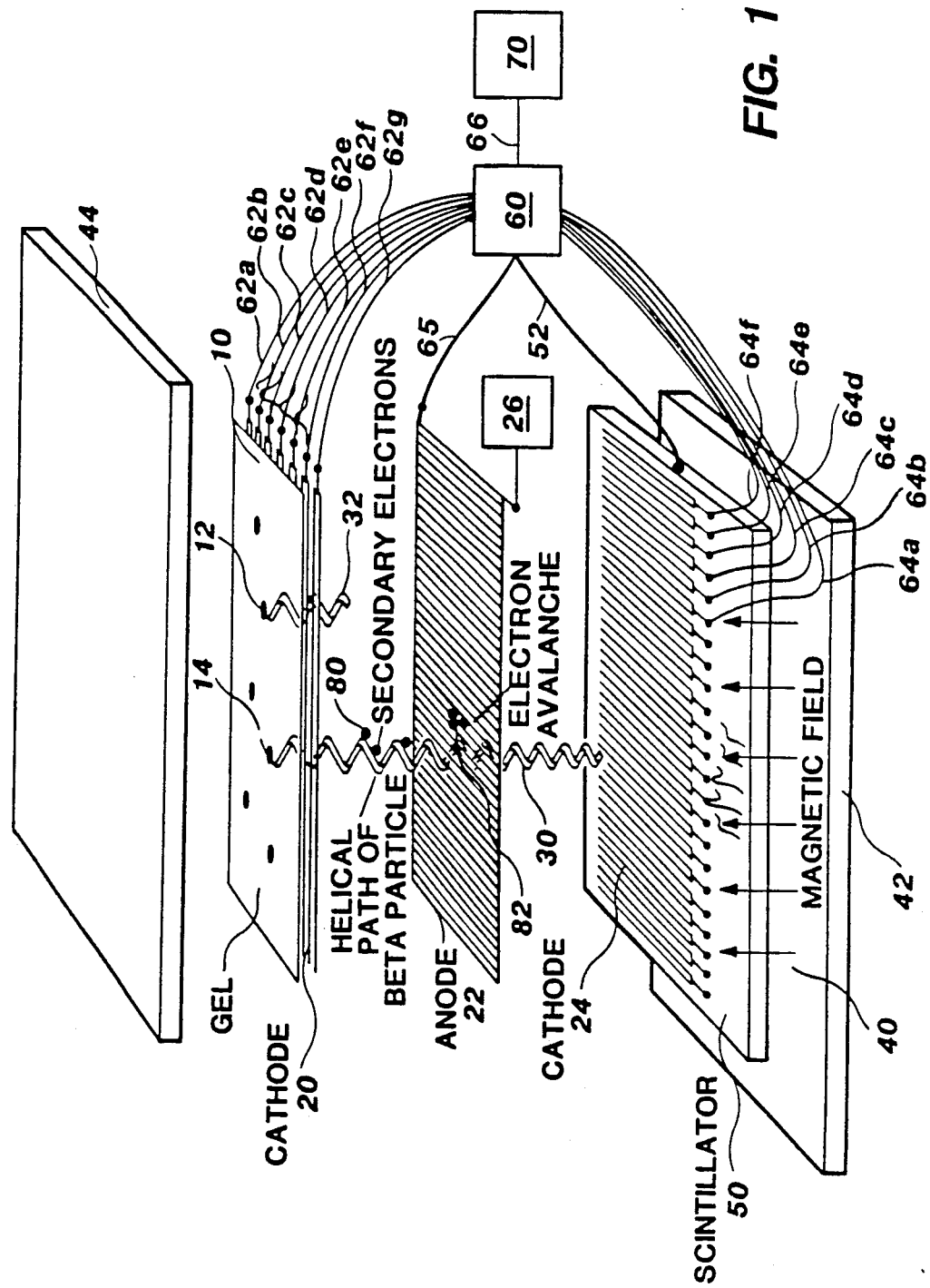
FIG. 1 is a schematic representation of the apparatus of the present invention showing the relative positions of the gel electrophoretogram, the two-dimensional readout cathode planes, the anode, the scintillator, and the magnetic field generating means for the preferred embodiment thereof.

Reference will now be made in detail to the present preferred embodiment of the invention, an example of which is illustrated in the accompanying drawings. Identical numerals are used to reference similar or corresponding structure throughout. Turning now to the drawings, FIG. 1 is a schematic representation of the apparatus of the present invention. A flat and rectangular gel electrophoretogram 10 having localized concentrations of β-ray-emitting compounds 12, is palced in close proximity to a multiwire proportional chamber which includes a first parallel wire cathode 20 (264, 100 μm dia. wires spaced 750 μm apart), a parallel wire anode 22 (128, 20 μm dia. wires, spaced 1500 μm apart) and second parallel wire cathode 24 (264, 100 μm dia. wires spaced 750 μm apart). Anode 22 was maintained at a 3000 V positive dc potential by voltage supply 26. The three planar wire electrodes 20, 22, 24, were spaced 4.8 mm apart and the planes disposed in a parallel manner. The two wire cathodes were oriented such that their wires were perpendicular and were operated near ground potential. Emitted β-rays 30, 32 were caused to follow helical paths by their interaction with an intense uniform magnetic field 40 of about 1.9 tesla generated between pole pieces 42, 44. A plastic scintillator, 50, 0.6 cm thick was located in close proximity to the wire proportional chamber and was designed to be insensitive to incident β-rays but to respond to cosmic rays entering the proportional chamber. Output 52 from the scintillator is directed to trigger means 60 as are the output 62 from the first wire cathode 20, the output 64 from the second cathode 24 and the output 65 from anode 22, the output 66 of which is in turn directed to an electronic counting and processing apparatus 70. As the β-rays pass into the proportional chamber they interact with a gas disposed therein which in particular pervades the region between the first cathode 20 and anode 22, and between the anode 22 and the second cathode 24. The interaction therebetween is principally twofold: first, the β-rays are slowed by collisions which monotonically reduce the radii of their helical paths, and second, each β-ray ionizes the gas, thereby producing secondary electrons 80 which, when accelerated toward the anode 22, generate individual electron avalanches 82. The multiplication factor is typically about 100,000, enough to produce a signal of several millivolts at the wire terminals. The cathode wires derive their signals by induction from the anode wires above or below them. In general, one β-ray will produce signals in only one anode wire, but in several cathode wires. Standard proportional gas mixtures of "magic" gas, 70% Ar. 29% isobutane, 0.6% Freon ®-13B1 (Freon ® is a registered trademark of the E. I. duPont de Nemours and Co.), and 0.4% methylal Mylar ® were employed. A slight flow at a pressure just above atmospheric pressure was maintained. The oxygen content was kept low in order to produce stable operation in the proportional chamber.

Figure 2:
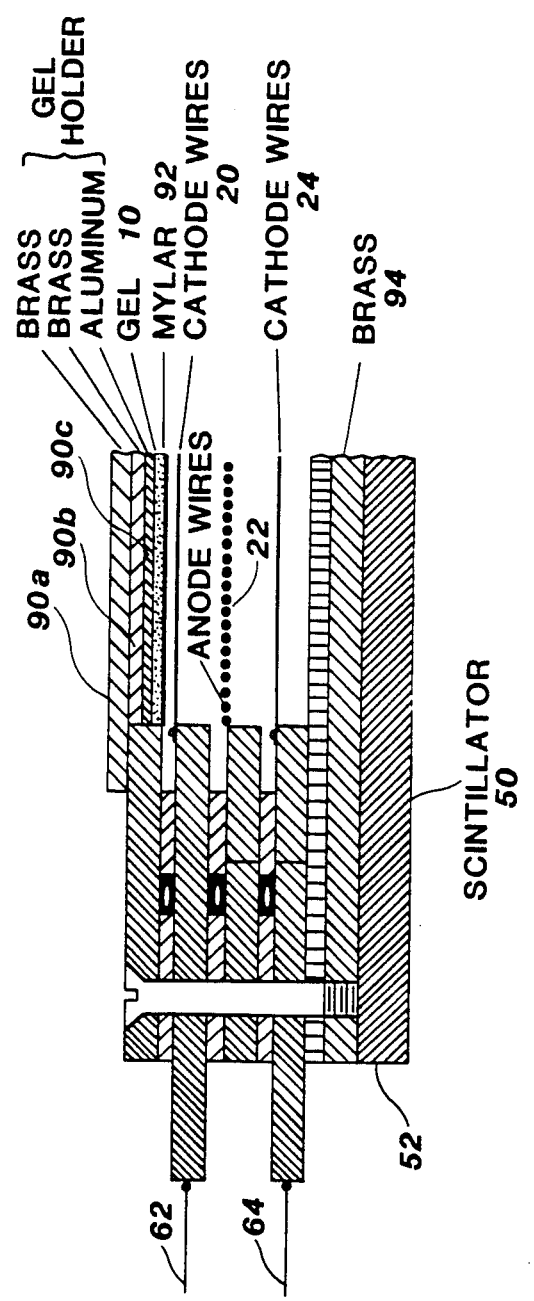
FIG. 2 is a more detailed schematic representation of the multiwire proportional chamber utilized to read flat, rectangular gel electrophoretograms in two dimensions according to the teachings of the present invention.

FIG. 2 is a more detailed schematic representation of the multiwire proportional chamber utilized to read flat, rectangular gel electrophoretograms. According to the teachings of the present inention, the gel electrophoretogram 10 was generally supported by a metal backplate 90 and placed substantially against a 6 μm thick aluminized (Mylar ® is a registered trademark of the E. I. duPont de Nemours and Co.) window 92, which forms part of the gas enclosure for the proportional chamber, in order to improve the resolution of the apparatus. A small negative bias was applied to the aluminized side of the window, which was located facing the inside of the chamber, in order to insure that electrons produced by ionization in the space between the Mylar ® window and the first cathode plane immediately next to it would drift into the active region of the chamber. Brass plate 94 prevents the scintillator 50 from interacting with the β-rays emitted from the gel and forms part of the gas enclosure for the proportional chamber. The total thickness of the proportional chamber was about 1 cm. Greater thickness would reduce the resoltuion of our apparatus. It should be mentioned that except in the situations where hard β-ray emitters are used to label the compounds separated by electrophoresis, such as $^{32}P$, the β-ray emission fromthe gel will occur only in one direction because of the metallic backplate used to support the gel. Therefore, in general, only one proportional chamber can be used to image the electrophoretogram. A general description of the cooperation among these elements will be set forth thereinbelow.

Figure 3:
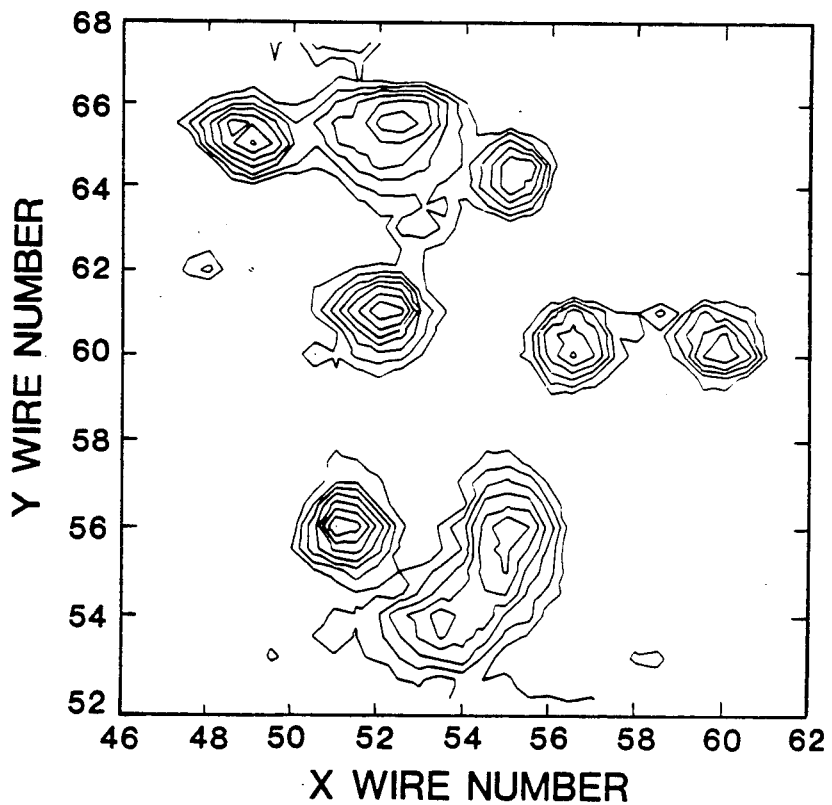
FIG. 3 shows a typical concentration pattern of β-ray-emitting labeled compounds on a gel electrophoretogram graphically displayed by the apparatus of the present invention.

FIG. 3 shows a typical concentration pattern of β-ray-emitting labeled compounds on a gel electrophoretogram graphically displayed using the apparatus of the present invention. Generally, such a pattern can be developed in less than one hour in situations where one has significant concentrations of labeled compounds and/or highly radioactive labeling nuclides.

The use of the magnetic field in the present invention is based on the principle that a low energy electron in a sufficiently strong magnetic field will follow a trajectory close to the fiel line that passes through its point of origin. For example, in a field of two tesla, a 50 keV β-ray, near the maximum of the $^{14}C$ spectrum, emitted at an angle of 30° with respect to the field direction, will keep within 400 μm of its field line. Lower energy electrons and those emitted at smaller angles follow the field lines even more closely. Moreover, as the β-rays are slowed by collisions with the detection gas present in the proportional chamber, the radius of their helical paths decreases. For example, the same 50 keV β-ray discussed hereinabove will typically make six revolutions as it crosses the 1 cm thickness of the proportional chamber utilized for the present measurements during which traverse its helical radius will decrease from about 300 to 230 μm. The energy lost in the collisions is about 27 keV which is sufficient to generate 1000 ion paris at the gas pressures employed. It is the recognition of this fact that enables high resolution reproduction of the two dimensional locations of concentrations of the labeled compounds in the gel to be achieved although the emitted β-rays emerge isotropically therefrom. To be observed is that the β-ray motion here is along the field lines rather than across them.

As mentioned, the β-rays produce ion pairs in the detection gas in the proportional chamber as they travel therethrough which ion pairs, when accelerated by the wire anode, cause avalances which induce charges on the nearby wire cathodes. The resulting signals identify the wires involved, thereby providing the two dimensional coordinates of the β-rays in the proportional chamber produced by each β-ray. The distribution for β-rays emitted from $^{14}C$ discussed in the previous paragraph has a full-width-at-half-maximum of about 700 μm which includes the effect of multiple scattering by the detection gas. This is smaller than the spot sizes under investigation which are generally between 1000 and 3000 μm. Better resoltuion may be achieved by using higher magnetic fields or changing the β-ray emitting species to, say, tritium which generates a lower energy β-ray. For measurements on tritium, however, it will be necessary to use a much thinner window or to position the gel inside the window.

In the present invention of a multiwire proportional chamber to the reading of gel electrophoretograms, a large number of closely spaced wires are employed to improve resolution, since the β-ray tracks do not cross many wires as they would do in the more usual situation where a proportional chamber is used to detect subatomic particles. According to the teachings of the present invention, the actuatl amplitudes of the signals on the cathode wires are not read in order to locate the centroid of the ionization. Rather, only the identiy of which of the closely spaced cathode wires is involved is determined. This procedure reduces the resolution, but considerably increases the speed of the measurements. For example, a single β-ray event can be processed within 30 μs.

Events of interest produce an avalanche on one or at most possibly two of the anode wires. This induces signals on those cathode wires that are closest to the avalanche. The trigger 60 is designed to recognize clusters of anode and cathode signals. Three coincidential clusters, one in x and one in y, as well as one bearing the proper amplitude appearing on the anode, are required. An accidental coincidence between two β-rays or between one β-ray and a noise spike will not be recorded if this produces more than one cluster in either cathode plane. An accidental coincidence between two β-rays arriving within the resolution time of the circuitry will not be recorded. If an odd number of wires is involved, the event is assigned the coordinate of the central wire. For an even number, the coordinate is defined to be halfway between the two principal wires. The trigger also incorporates a veto for cosmic rays detected by the scintillation counter. This protects against cosmic rays coming from both above and below; those entering the side will give a characteristic multiwire signal that will not satisfy the trigger.

A computer accumulates the counts at each location directly in digital form. In the present design, an area 19.2 cm×19.2 cm is covered. The events are summed in 65,536 bins, each 750 microns×750 microns in area. Since the data can be collected at th reate of 30,000 events per second and the backgroun is low, the system is capable of spanning a high dynamic range in a relatively short time. The present radout system can electronically distinguish $^{3}H$ from $^{14}C$ when these nuclides are simultaneously employed as radionuclide labels. This is achieved by investigating the pulse height of the anode signal appearing on output 65. The two β-ray-emitting nuclides emit these particles with very different energy spectra which are readily distinguishable by the characteristics of the avalanche produced thereby. It should be mentioned that the detection gas mixture may have to be adjusted to maximize the differences in ionization generated therein by the different energy β-rays.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What we claim is:

1. An apparatus for reading flat, substantially planar two-dimensional gel electrophoretograms containing β-ray-emitting labeled compounds, said apparatus comprising in combination:

a. a single, substantially flat and rectangular proportional chamber radiation detection means substantially parallel to and approximately coextensive with the gel electrophoretogram for receiving β-rays emitted from the electrophoretogram and cosmic rays and generating electrical signals according to the two dimensional coordinates of each β-ray and cosmic ray received thereby, said substantially flat and rectangular proportional chamber radiation detector means being located in close proximity to the gel surface and containing a β-radiation detection gas;

b. substantially flat and rectangular scintillator means located nearby to said substantially flat and rectangular proportional chamber radiation detection means for detecting the incidence of cosmic rays on said substantially flat and rectangular proportional chamber radiation detection means and having an electrical output in response thereto, yet having substantially no sensitivity to the β-rays emitted from the gel, said substantially flat and rectangular scintillator means being disposed in a substantially parallel manner thereto and being substantially coextensive therewith, such that the electrical signals generated from said flat, rectangular proportional chamber means may be related substantially solely to the two dimensional coordinates of the β-rays incident thereon; and c. magnetic field generating means for providing a substantially uniform magnetic field having dimensions substantially coextensive with the rectangular dimension of said substantially flat and rectangular proportional chamber radiation detection means and passing substantially perpendicularly therethrough and through said scintillator means, the magnetic field generated therefrom having sufficient magnitude to cause the β-rays emitted from the gel in the direction of said substantially flat and rectangular proportional chamber means to move in an increasingly tight helical path therein as the emitted β-rays are slowed by collisions with the β-radiation detection gas, so as to substantially retin the two dimensional coordinate information of their origin within the gel.

2. The apparatus as described in claim 1, wherein said substantially flat and rectangular proportional chamber radiation detection means includes a multiwire proportional chamber comprising in combination:

i. a β-ray transmitting window located in close proximity to and substantially parallel to the substantially planar, two-dimensional gel electrophoretogram, said β-ray transmitting window being approximately coextensive therewith;

ii. a first substantially planar plurality of parallel wires disposed in close proximity to said β-ray transmitting window approximately coextensive therewith and substantially parallel thereto, each of said wires comprising said first substantially planar plurality of parallel wires being in substantial electrical isolation from any of the other wires of said first substantially planar plurality of parallel wires and having an individual electrical output;

iii. a second substantially planar plurality of wires substantially parallel to said first planar plurality of parallel wires and substantially coextensive therwith disposed in close proximity to said first substantially planar plurality of wires on the side thereof away from said β-ray transmitting window, each of said wires comprising said second substantially planar plurality of wires being in electrical contact with all of the other wires comprising said second substantially planar plurality of parallel wires, said second substantially planar plurality of parallel wires having an electrical output and being biased at a high positie voltage relative to ground; and iv. a third substantially planar plurality of parallel wires disposed in close proximity to said second substantially planar plurality of parallel wires on the side thereof away from said first substantially planar plurality of parallel wires, approximately coextensive therewith and substantially parallel thereto, each of said wires comprising said third substantially planar plurality of parallel wires being in substantial electricl isolation from any of the other wires of said third substantially planar plurality of parallel wires and having an individual electrical output, each of said wires comprising said third substantially planar plurality of parallel wires being disposed in a substantially perpendicular manner to each of said wires comprising said first substantially planar plurality of wires.

3. The apparatus as described in claim 2, further comprising trigger means and electronic counting and processing means, said trigger means being responsive to said individual electrical output from each of said wires comprising said first substantially planar plurality of parallelw ires, to said individual electrical output from each of said wires comprising said third substantially planar plurality of parallel wires, to said electrical output from said second substantially planar plurality of parallel wires, and to said electrical output from said substantially flat and rectangular scintillator means, such that said trigger means is itsel activated and in turn permits said electrical counting and processing means to receive the electrical output from certain of said wires from said first substantially planar plurality of prallel wires, the electrical output of certain of said wires from said third substantially planar plurality of parallelw ires and the electrical output from said second substantially planar plurality of prallel wires, so as to determine the two dimensional coordinates in the two-dimensional gel electrophoretogram of each of the β-rays causing an avalanche, when, in response to avalanches generated by emitted β-rays interacting with the detection gas, electrical signals are induced substantiallysimultaneously on certain of said wires of said first substantially planar plurality of prallel wires, on certain of said wires of said third substantially planar plurality of parallel wires and on said second substantially planar plurality of parallel wires, the activation of said trigge rmeans being avoided when a substantial temporal coincidence occurs between a β-ray induced avalanche and any of an electrical signal produced by a cosmic ray on said substantially flat and rectangular scintillation means and a second β-ray induced avalanche and when the electrical output from said second substantially planar plurality of parallel wires is outside of a chosen range.

4. The apparatus as described in claim 3, wherein said β-radiation detection gas consists essentially of "magic" gas.

5. The apparatus as described in claim 1, wherein said substantially flat and rectangular proportional chamber radiation detection means is interposed between the substantially planar, two-dimensional gel electrophoretogram and said scintillator means.

6. The apparatus as described in claim 1, further comprising means for determining the energy of the β-rays entering said substantially flat and rectangular proportional chamber radiation detection means, so as to permit said apparatus to distinguish among a plurality of β-ray-emitting labeling nuclei used for labeling the compounds in the gel electrophoretogram.

7. A method of reading flat two-dimensional gel electrophoretograms containing $\beta$-ray-emitting labeled compounds, said method comprising the steps of:
  a. placing the gel electrophoretogram in a uniform strong magnetic field such that emitted $\beta$-rays execute tight helical motion as they travel in the direction of the magnetic field lines so as to substantially preserve the original two dimensional coordinates in the gel thereof; and
  b. electronically detecting each of the $\beta$-rays emerging from only one side of the gel electrophoretogram, so as to produce an intensity distribution of the two dimensional coordinates thereof which can be related to the origin of the $\beta$-rays in the gel electrophoretogram and consequently to the location and intensity of the labeled compounds therein.

8. The method as described in claim 7, further comprising the step of interacting the emitted $\beta$-rays with a gas, such that a plurality of charged particles are formed therein, and such that the $\beta$-rays travel in helices having decreasing radii as a result of the loss of energy thereof through collisions with the gas.

9. The method as described in claim 8, further comprising the step of accelerating the plurality of charges formed according to the step described in claim 7 in order to produce an electron avalanche, so as to assist in said step of electronically detecting each of the $\beta$-rays.

10. The method as described in claim 9, further comprising the step of correcting the intensity distribution generated in step b for effects produced by cosmic rays.

11. The method as described in claim 10, further comprising the step of determining the energy of each of the $\beta$-rays in order that a plurality of distinct $\beta$-ray-emitting radioactive labeling nuclei can be used to label the compounds in the gel electrophoretogram.

* * * * *